(12) United States Patent
Scirica et al.

(10) Patent No.: US 8,127,976 B2
(45) Date of Patent: Mar. 6, 2012

(54) STAPLER CARTRIDGE AND CHANNEL INTERLOCK

(75) Inventors: Paul Scirica, Huntington, CT (US); Lee Olson, Wallingford, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 196 days.

(21) Appl. No.: 12/437,709

(22) Filed: May 8, 2009

(65) Prior Publication Data

US 2010/0282816 A1 Nov. 11, 2010

(51) Int. Cl.
*B21J 15/28* (2006.01)
*B27F 7/17* (2006.01)
*A61B 17/04* (2006.01)
*A61B 17/10* (2006.01)

(52) U.S. Cl. .... 227/176.1; 227/8; 227/178.1; 227/180.1

(58) Field of Classification Search ............... 227/178.1, 227/176.1, 180.1, 175.1, 8; 606/142, 143, 606/219; 403/348–349
See application file for complete search history.

(56) References Cited

U.S. PATENT DOCUMENTS

| | | | |
|---|---|---|---|
| 3,079,606 A | 3/1963 | Bobrov et al. | |
| 3,490,675 A | 1/1970 | Green et al. | |
| 3,777,538 A | 12/1973 | Weatherly et al. | |
| 3,882,854 A | 5/1975 | Hulka et al. | |
| 4,027,510 A | 6/1977 | Hiltebrandt | |
| 4,086,926 A | 5/1978 | Green et al. | |
| 4,244,372 A | 1/1981 | Kapitanov et al. | |
| 4,429,695 A | 2/1984 | Green | |
| 4,505,414 A | 3/1985 | Filipi | |
| 4,520,817 A | 6/1985 | Green | |
| 4,589,413 A | 5/1986 | Malyshev et al. | |
| 4,596,351 A | 6/1986 | Fedotov et al. | |
| 4,602,634 A | 7/1986 | Barkley | |
| 4,605,001 A | 8/1986 | Rothfuss et al. | |
| 4,608,981 A | 9/1986 | Rothfuss et al. | |
| 4,610,383 A | 9/1986 | Rothfuss et al. | |
| 4,633,861 A | 1/1987 | Chow et al. | |
| 4,633,874 A | 1/1987 | Chow et al. | |
| 4,637,395 A * | 1/1987 | Caspar et al. | 606/143 |
| 4,671,445 A | 6/1987 | Barker et al. | |
| 4,700,703 A | 10/1987 | Resnick et al. | |
| 4,703,887 A | 11/1987 | Clanton et al. | |
| 4,728,020 A | 3/1988 | Green et al. | |
| 4,752,024 A | 6/1988 | Green et al. | |

(Continued)

FOREIGN PATENT DOCUMENTS

AU 5476586 9/1986

(Continued)

OTHER PUBLICATIONS

European Search Report for EP 10 25 0889 date of completion is Aug. 24, 2010 (3 pages).

*Primary Examiner* — Rinaldi Rada
*Assistant Examiner* — Robert Long (57) ABSTRACT

A surgical stapling device including a handle assembly, an endoscopic portion and an end effector is disclosed. The endoscopic portion extends distally from the handle assembly and defines a first longitudinal axis. The end effector defines a second longitudinal axis and includes an anvil assembly and a cartridge assembly. The end effector includes a cartridge channel configured and dimensioned to securely receive a cartridge therein.

8 Claims, 4 Drawing Sheets

U.S. PATENT DOCUMENTS

| | | | |
|---|---|---|---|
| 4,784,137 A | 11/1988 | Kulik et al. | |
| 4,863,088 A | 9/1989 | Redmond et al. | |
| 4,869,415 A | 9/1989 | Fox | |
| 4,892,244 A | 1/1990 | Fox et al. | |
| 4,955,959 A | 9/1990 | Tompkins et al. | |
| 4,978,049 A | 12/1990 | Green | |
| 4,991,764 A | 2/1991 | Mericle | |
| 5,014,899 A | 5/1991 | Presty et al. | |
| 5,031,814 A | 7/1991 | Tompkins et al. | |
| 5,040,715 A | 8/1991 | Green et al. | |
| 5,065,929 A | 11/1991 | Schulze et al. | |
| 5,071,430 A | 12/1991 | deSalis et al. | |
| 5,074,454 A | 12/1991 | Peters | |
| 5,083,695 A | 1/1992 | Foslien et al. | |
| 5,084,057 A | 1/1992 | Green et al. | |
| 5,106,008 A | 4/1992 | Tompkins et al. | |
| 5,111,987 A | 5/1992 | Moeinzadeh et al. | |
| 5,129,570 A | 7/1992 | Schulze et al. | |
| 5,141,144 A | 8/1992 | Foslien et al. | |
| 5,156,315 A | 10/1992 | Green et al. | |
| 5,156,614 A | 10/1992 | Green et al. | |
| 5,163,943 A | 11/1992 | Mohiuddin et al. | |
| 5,170,925 A | 12/1992 | Madden et al. | |
| 5,171,247 A | 12/1992 | Hughetti et al. | |
| 5,173,133 A | 12/1992 | Morin et al. | |
| 5,180,092 A | 1/1993 | Crainich | |
| 5,188,274 A | 2/1993 | Moeinzadeh et al. | |
| 5,220,928 A | 6/1993 | Oddsen et al. | |
| 5,221,036 A | 6/1993 | Takase | |
| 5,242,457 A | 9/1993 | Akopov et al. | |
| 5,246,156 A | 9/1993 | Rothfuss et al. | |
| 5,253,793 A | 10/1993 | Green et al. | |
| 5,263,629 A | 11/1993 | Trumbull et al. | |
| RE34,519 E | 1/1994 | Fox et al. | |
| 5,275,323 A | 1/1994 | Schulze et al. | |
| 5,282,807 A | 2/1994 | Knoepfler | |
| 5,289,963 A | 3/1994 | McGarry et al. | |
| 5,307,976 A | 5/1994 | Olson et al. | |
| 5,308,576 A | 5/1994 | Green et al. | |
| 5,312,023 A | 5/1994 | Green et al. | |
| 5,318,221 A | 6/1994 | Green et al. | |
| 5,326,013 A | 7/1994 | Green et al. | |
| 5,328,077 A | 7/1994 | Lou | |
| 5,330,486 A | 7/1994 | Wilk | |
| 5,332,142 A | 7/1994 | Robinson et al. | |
| 5,336,232 A | 8/1994 | Green et al. | |
| 5,344,061 A | 9/1994 | Crainich | |
| 5,352,238 A | 10/1994 | Green et al. | |
| 5,356,064 A | 10/1994 | Green et al. | |
| 5,358,506 A | 10/1994 | Green et al. | |
| 5,364,001 A | 11/1994 | Bryan | |
| 5,364,002 A | 11/1994 | Green et al. | |
| 5,364,003 A | 11/1994 | Williamson, IV | |
| 5,366,133 A | 11/1994 | Geiste | |
| 5,376,095 A | 12/1994 | Ortiz | |
| 5,379,933 A | 1/1995 | Green et al. | |
| 5,381,943 A | 1/1995 | Allen et al. | |
| 5,382,255 A | 1/1995 | Castro et al. | |
| 5,383,880 A | 1/1995 | Hooven | |
| 5,395,033 A | 3/1995 | Byrne et al. | |
| 5,395,034 A | 3/1995 | Allen et al. | |
| 5,397,046 A | 3/1995 | Savage et al. | |
| 5,397,324 A | 3/1995 | Carroll et al. | |
| 5,405,072 A | 4/1995 | Zlock et al. | |
| 5,407,293 A | 4/1995 | Crainich | |
| 5,413,268 A | 5/1995 | Green et al. | |
| 5,415,334 A | 5/1995 | Williamson, IV et al. | |
| 5,415,335 A | 5/1995 | Knodell, Jr. | |
| 5,417,361 A | 5/1995 | Williamson, IV | |
| 5,423,471 A | 6/1995 | Mastri et al. | |
| 5,425,745 A | 6/1995 | Green et al. | |
| 5,431,322 A | 7/1995 | Green et al. | |
| 5,431,323 A | 7/1995 | Smith et al. | |
| 5,433,721 A | 7/1995 | Hooven et al. | |
| 5,441,193 A | 8/1995 | Gravener | |
| 5,445,304 A | 8/1995 | Plyley et al. | |
| 5,447,265 A | 9/1995 | Vidal et al. | |
| 5,452,837 A | 9/1995 | Williamson, IV et al. | |
| 5,456,401 A | 10/1995 | Green et al. | |
| 5,464,300 A | 11/1995 | Crainich | |
| 5,465,895 A | 11/1995 | Knodel et al. | |
| 5,467,911 A | 11/1995 | Tsuruta et al. | |
| 5,470,006 A * | 11/1995 | Rodak | 227/176.1 |
| 5,470,007 A | 11/1995 | Plyley et al. | |
| 5,470,010 A | 11/1995 | Rothfuss et al. | |
| 5,472,132 A | 12/1995 | Savage et al. | |
| 5,474,566 A | 12/1995 | Alesi et al. | |
| 5,476,206 A | 12/1995 | Green et al. | |
| 5,478,003 A | 12/1995 | Green et al. | |
| 5,480,089 A | 1/1996 | Blewett | |
| 5,482,197 A | 1/1996 | Green et al. | |
| 5,484,095 A | 1/1996 | Green et al. | |
| 5,484,451 A | 1/1996 | Akopov et al. | |
| 5,485,947 A | 1/1996 | Olson et al. | |
| 5,485,952 A | 1/1996 | Fontayne | |
| 5,486,185 A | 1/1996 | Freitas et al. | |
| 5,487,499 A | 1/1996 | Sorrentino et al. | |
| 5,487,500 A | 1/1996 | Knodel et al. | |
| 5,489,058 A | 2/1996 | Plyley et al. | |
| 5,490,856 A | 2/1996 | Person et al. | |
| 5,497,933 A | 3/1996 | DeFonzo et al. | |
| 5,501,689 A | 3/1996 | Green et al. | |
| 5,505,363 A | 4/1996 | Green et al. | |
| 5,507,426 A | 4/1996 | Young et al. | |
| 5,518,163 A | 5/1996 | Hooven | |
| 5,518,164 A | 5/1996 | Hooven | |
| 5,529,235 A | 6/1996 | Boiarski et al. | |
| 5,531,744 A | 7/1996 | Nardella et al. | |
| 5,535,934 A | 7/1996 | Boiarski et al. | |
| 5,535,935 A | 7/1996 | Vidal et al. | |
| 5,535,937 A | 7/1996 | Boiarski et al. | |
| 5,540,375 A | 7/1996 | Bolanos et al. | |
| 5,542,594 A | 8/1996 | McKean et al. | |
| 5,549,628 A | 8/1996 | Cooper et al. | |
| 5,551,622 A | 9/1996 | Yoon | |
| 5,553,765 A | 9/1996 | Knodel et al. | |
| 5,554,164 A | 9/1996 | Wilson et al. | |
| 5,554,169 A | 9/1996 | Green et al. | |
| 5,560,530 A | 10/1996 | Bolanos et al. | |
| 5,560,532 A | 10/1996 | DeFonzo et al. | |
| 5,562,239 A | 10/1996 | Boiarski et al. | |
| 5,562,241 A | 10/1996 | Knodel et al. | |
| 5,562,682 A | 10/1996 | Oberlin et al. | |
| 5,562,701 A | 10/1996 | Huitema et al. | |
| 5,564,615 A | 10/1996 | Bishop et al. | |
| 5,571,116 A | 11/1996 | Bolanos et al. | |
| 5,573,169 A | 11/1996 | Green et al. | |
| 5,573,543 A | 11/1996 | Akopov et al. | |
| 5,575,799 A | 11/1996 | Bolanos et al. | |
| 5,575,803 A | 11/1996 | Cooper et al. | |
| 5,577,654 A | 11/1996 | Bishop | |
| 5,579,107 A | 11/1996 | Wright et al. | |
| 5,584,425 A | 12/1996 | Savage et al. | |
| 5,586,711 A | 12/1996 | Plyley et al. | |
| 5,588,580 A | 12/1996 | Paul et al. | |
| 5,588,581 A | 12/1996 | Conlon et al. | |
| 5,597,107 A | 1/1997 | Knodel et al. | |
| 5,601,224 A | 2/1997 | Bishop et al. | |
| 5,607,095 A | 3/1997 | Smith et al. | |
| 5,615,820 A | 4/1997 | Viola | |
| 5,618,291 A | 4/1997 | Thompson et al. | |
| 5,624,452 A | 4/1997 | Yates | |
| 5,626,587 A | 5/1997 | Bishop et al. | |
| 5,628,446 A | 5/1997 | Geiste et al. | |
| 5,630,539 A | 5/1997 | Plyley et al. | |
| 5,630,540 A | 5/1997 | Blewett | |
| 5,630,541 A | 5/1997 | Williamson, IV et al. | |
| 5,632,432 A | 5/1997 | Schulze et al. | |
| 5,634,584 A | 6/1997 | Okorocha et al. | |
| 5,636,780 A | 6/1997 | Green et al. | |
| 5,645,209 A | 7/1997 | Green et al. | |
| 5,647,526 A | 7/1997 | Green et al. | |
| 5,651,491 A | 7/1997 | Heaton et al. | |
| 5,653,373 A | 8/1997 | Green et al. | |
| 5,653,374 A | 8/1997 | Young et al. | |
| 5,653,721 A | 8/1997 | Knodel et al. | |
| 5,655,698 A | 8/1997 | Yoon | |

| | | | | | | |
|---|---|---|---|---|---|---|
| 5,657,921 A | 8/1997 | Young et al. | | 5,941,442 A | 8/1999 | Geiste et al. |
| 5,658,300 A | 8/1997 | Bito et al. | | 5,954,259 A | 9/1999 | Viola et al. |
| 5,662,258 A | 9/1997 | Knodel et al. | | 5,980,510 A | 11/1999 | Tsonton et al. |
| 5,662,259 A | 9/1997 | Yoon | | 5,988,479 A | 11/1999 | Palmer |
| 5,662,260 A | 9/1997 | Yoon | | 6,004,335 A | 12/1999 | Vaitekunas et al. |
| 5,662,662 A | 9/1997 | Bishop et al. | | 6,010,054 A | 1/2000 | Johnson et al. |
| 5,662,666 A | 9/1997 | Onuki et al. | | 6,032,849 A | 3/2000 | Mastri et al. |
| 5,665,085 A | 9/1997 | Nardella | | 6,045,560 A | 4/2000 | McKean et al. |
| 5,667,517 A | 9/1997 | Hooven | | 6,063,097 A | 5/2000 | Oi et al. |
| 5,669,544 A | 9/1997 | Schulze et al. | | 6,079,606 A | 6/2000 | Milliman et al. |
| 5,673,840 A | 10/1997 | Schulze et al. | | 6,099,551 A | 8/2000 | Gabbay |
| 5,673,841 A | 10/1997 | Schulze et al. | | 6,109,500 A | 8/2000 | Alli et al. |
| 5,673,842 A | 10/1997 | Bittner et al. | | 6,131,789 A | 10/2000 | Schulze et al. |
| 5,676,674 A | 10/1997 | Bolanos et al. | | 6,131,790 A | 10/2000 | Piraka |
| 5,680,981 A | 10/1997 | Mililli et al. | | 6,155,473 A | 12/2000 | Tompkins et al. |
| 5,680,982 A | 10/1997 | Schulze et al. | | 6,197,017 B1 | 3/2001 | Brock et al. |
| 5,690,269 A | 11/1997 | Bolanos et al. | | 6,202,914 B1 | 3/2001 | Geiste et al. |
| 5,692,668 A | 12/1997 | Schulze et al. | | 6,241,139 B1 | 6/2001 | Milliman et al. |
| 5,697,542 A | 12/1997 | Knodel et al. | | 6,250,532 B1 | 6/2001 | Green et al. |
| 5,702,409 A | 12/1997 | Rayburn et al. | | 6,264,086 B1 | 7/2001 | McGuckin, Jr. |
| 5,704,534 A | 1/1998 | Huitema et al. | | 6,264,087 B1 | 7/2001 | Whitman |
| 5,706,997 A | 1/1998 | Green et al. | | 6,269,977 B1 | 8/2001 | Moore |
| 5,709,334 A | 1/1998 | Sorrentino et al. | | 6,279,809 B1 | 8/2001 | Nicolo |
| 5,711,472 A | 1/1998 | Bryan | | 6,315,183 B1 | 11/2001 | Piraka |
| 5,713,505 A | 2/1998 | Huitema | | 6,315,184 B1 | 11/2001 | Whitman |
| 5,715,988 A | 2/1998 | Palmer | | 6,325,810 B1 | 12/2001 | Hamilton et al. |
| 5,716,366 A | 2/1998 | Yates | | 6,330,965 B1 | 12/2001 | Milliman et al. |
| 5,718,359 A | 2/1998 | Palmer | | 6,391,038 B2 | 5/2002 | Vargas et al. |
| 5,725,536 A | 3/1998 | Oberlin et al. | | 6,398,797 B2 | 6/2002 | Bombard et al. |
| 5,725,554 A | 3/1998 | Simon et al. | | 6,436,097 B1 | 8/2002 | Nardella |
| 5,728,110 A | 3/1998 | Vidal et al. | | 6,439,446 B1 | 8/2002 | Perry et al. |
| 5,732,806 A | 3/1998 | Foshee et al. | | 6,443,973 B1 | 9/2002 | Whitman |
| 5,735,848 A | 4/1998 | Yates et al. | | 6,463,623 B2 | 10/2002 | Ahn et al. |
| 5,743,456 A | 4/1998 | Jones et al. | | 6,478,804 B2 | 11/2002 | Vargas et al. |
| 5,749,893 A | 5/1998 | Vidal et al. | | 6,488,196 B1 | 12/2002 | Fenton, Jr. |
| 5,752,644 A | 5/1998 | Bolanos et al. | | 6,503,257 B2 | 1/2003 | Grant et al. |
| 5,762,255 A | 6/1998 | Chrisman et al. | | 6,505,768 B2 | 1/2003 | Whitman |
| 5,762,256 A * | 6/1998 | Mastri et al. ............... 227/176.1 | | 6,544,274 B2 | 4/2003 | Danitz et al. |
| 5,769,303 A | 6/1998 | Knodel et al. | | 6,554,844 B2 | 4/2003 | Lee et al. |
| 5,769,892 A | 6/1998 | Kingwell | | 6,565,554 B1 | 5/2003 | Niemeyer |
| 5,772,099 A | 6/1998 | Gravener | | 6,587,750 B2 | 7/2003 | Gerbi et al. |
| 5,772,673 A | 6/1998 | Cuny et al. | | 6,592,597 B2 | 7/2003 | Grant et al. |
| 5,779,130 A | 7/1998 | Alesi et al. | | 6,594,552 B1 | 7/2003 | Nowlin et al. |
| 5,779,131 A | 7/1998 | Knodel et al. | | 6,602,252 B2 | 8/2003 | Mollenauer |
| 5,779,132 A | 7/1998 | Knodel et al. | | 6,612,053 B2 | 9/2003 | Liao |
| 5,782,396 A | 7/1998 | Mastri et al. | | 6,619,529 B2 | 9/2003 | Green et al. |
| 5,782,397 A | 7/1998 | Koukline | | 6,644,532 B2 | 11/2003 | Green et al. |
| 5,782,834 A | 7/1998 | Lucey et al. | | 6,656,193 B2 | 12/2003 | Grant et al. |
| 5,785,232 A | 7/1998 | Vidal et al. | | 6,669,073 B2 | 12/2003 | Milliman et al. |
| 5,797,536 A | 8/1998 | Smith et al. | | 6,681,978 B2 * | 1/2004 | Geiste et al. ............... 227/176.1 |
| 5,797,537 A | 8/1998 | Oberlin et al. | | 6,698,643 B2 | 3/2004 | Whitman |
| 5,797,538 A | 8/1998 | Heaton et al. | | 6,716,232 B1 | 4/2004 | Vidal et al. |
| 5,810,811 A | 9/1998 | Yates et al. | | 6,722,552 B2 | 4/2004 | Fenton, Jr. |
| 5,810,855 A | 9/1998 | Rayburn et al. | | 6,731,473 B2 | 5/2004 | Li et al. |
| 5,814,055 A * | 9/1998 | Knodel et al. ............... 606/151 | | 6,755,338 B2 | 6/2004 | Hahnen et al. |
| 5,814,057 A | 9/1998 | Oi et al. | | 6,783,524 B2 | 8/2004 | Anderson et al. |
| 5,816,471 A | 10/1998 | Plyley et al. | | 6,786,382 B1 | 9/2004 | Hoffman |
| 5,817,109 A | 10/1998 | McGarry et al. | | 6,808,262 B2 | 10/2004 | Chapoy et al. |
| 5,820,009 A | 10/1998 | Melling et al. | | 6,817,509 B2 * | 11/2004 | Geiste et al. ............... 227/176.1 |
| 5,823,066 A | 10/1998 | Huitema et al. | | 6,830,174 B2 | 12/2004 | Hillstead et al. |
| 5,826,776 A | 10/1998 | Schulze et al. | | 6,835,199 B2 | 12/2004 | McGuckin, Jr. et al. |
| 5,829,662 A | 11/1998 | Allen et al. | | 6,843,403 B2 | 1/2005 | Whitman |
| 5,833,695 A | 11/1998 | Yoon | | RE38,708 E | 3/2005 | Bolanos et al. |
| 5,836,147 A | 11/1998 | Schnipke | | 6,877,647 B2 | 4/2005 | Green et al. |
| 5,862,972 A | 1/1999 | Green et al. | | 6,879,880 B2 | 4/2005 | Nowlin et al. |
| 5,865,361 A | 2/1999 | Milliman et al. | | 6,889,116 B2 | 5/2005 | Jinno |
| 5,871,135 A | 2/1999 | Williamson, IV et al. | | 6,905,057 B2 | 6/2005 | Swayze et al. |
| 5,873,873 A | 2/1999 | Smith et al. | | 6,953,138 B1 | 10/2005 | Dworak et al. |
| 5,878,938 A | 3/1999 | Bittner et al. | | 6,953,139 B2 | 10/2005 | Milliman et al. |
| 5,893,506 A | 4/1999 | Powell | | 6,959,852 B2 | 11/2005 | Shelton, IV et al. |
| 5,894,979 A | 4/1999 | Powell | | 6,962,594 B1 | 11/2005 | Thevenet |
| 5,897,562 A | 4/1999 | Bolanos et al. | | 6,964,363 B2 | 11/2005 | Wales et al. |
| 5,901,895 A | 5/1999 | Heaton et al. | | 6,978,921 B2 | 12/2005 | Shelton, IV et al. |
| 5,911,352 A | 6/1999 | Racenet et al. | | 6,981,628 B2 | 1/2006 | Wales |
| 5,911,353 A * | 6/1999 | Bolanos et al. ............ 227/180.1 | | 6,986,451 B1 | 1/2006 | Mastri et al. |
| 5,918,791 A | 7/1999 | Sorrentino et al. | | 6,988,649 B2 | 1/2006 | Shelton, IV et al. |
| 5,919,198 A | 7/1999 | Graves, Jr. et al. | | 6,991,627 B2 | 1/2006 | Madhani et al. |
| 5,922,001 A | 7/1999 | Yoon | | 6,994,714 B2 | 2/2006 | Vargas et al. |
| 5,931,847 A | 8/1999 | Bittner et al. | | 7,000,818 B2 | 2/2006 | Shelton, IV et al. |

| Patent No. | Date | Inventor(s) |
|---|---|---|
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,724 B2 | 11/2007 | Green et al. |
| 7,296,772 B2 | 11/2007 | Wang |
| 7,300,444 B1 | 11/2007 | Nielsen et al. |
| 7,303,108 B2 | 12/2007 | Shelton, IV |
| 7,308,998 B2 | 12/2007 | Mastri et al. |
| 7,328,828 B2 | 2/2008 | Ortiz et al. |
| 7,328,829 B2 | 2/2008 | Arad et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,399,310 B2 | 7/2008 | Edoga et al. |
| 7,401,720 B1 | 7/2008 | Durrani |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,495 B2 | 9/2008 | Menn et al. |
| 7,422,139 B2 | 9/2008 | Shelton, IV et al. |
| 7,431,189 B2 | 10/2008 | Shelton, IV et al. |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,559,453 B2 * | 7/2009 | Heinrich et al. ............ 227/180.1 |
| 7,637,410 B2 * | 12/2009 | Marczyk ..................... 227/175.2 |
| 7,762,445 B2 * | 7/2010 | Heinrich et al. ............ 227/180.1 |
| 7,845,535 B2 * | 12/2010 | Scircia ........................ 227/176.1 |
| 7,913,893 B2 * | 3/2011 | Mastri et al. ................ 227/176.1 |
| 7,950,562 B2 * | 5/2011 | Beardsley et al. .......... 227/176.1 |
| 2002/0004498 A1 | 1/2002 | Doherty |
| 2002/0009193 A1 | 1/2002 | Deguchi |
| 2002/0018323 A1 | 2/2002 | Li |
| 2002/0032948 A1 | 3/2002 | Ahn |
| 2002/0036748 A1 | 3/2002 | Chapoy |
| 2002/0045442 A1 | 4/2002 | Silen et al. |
| 2002/0069595 A1 | 6/2002 | Knudson et al. |
| 2002/0084304 A1 | 7/2002 | Whitman |
| 2002/0111621 A1 | 8/2002 | Wallace et al. |
| 2002/0143346 A1 | 10/2002 | McGuckin, Jr. et al. |
| 2002/0177843 A1 | 11/2002 | Anderson et al. |
| 2002/0188294 A1 | 12/2002 | Couture et al. |
| 2002/0190093 A1 | 12/2002 | Fenton, Jr. |
| 2003/0009193 A1 | 1/2003 | Corsaro |
| 2003/0105476 A1 | 6/2003 | Sancoff et al. |
| 2003/0132268 A1 | 7/2003 | Whitman |
| 2004/0004105 A1 | 1/2004 | Jankowski |
| 2004/0007608 A1 | 1/2004 | Ehrenfels et al. |
| 2004/0050902 A1 | 3/2004 | Green |
| 2004/0093029 A1 | 5/2004 | Zubik et al. |
| 2004/0094597 A1 | 5/2004 | Whitman |
| 2004/0094598 A1 * | 5/2004 | Geiste et al. ................ 227/180.1 |
| 2004/0108357 A1 | 6/2004 | Milliman |
| 2004/0149802 A1 | 8/2004 | Whitman |
| 2004/0173659 A1 | 9/2004 | Green |
| 2004/0199180 A1 | 10/2004 | Knodel et al. |
| 2004/0199181 A1 | 10/2004 | Knodel et al. |
| 2004/0232199 A1 | 11/2004 | Shelton, IV et al. |
| 2004/0232200 A1 | 11/2004 | Shelton, IV et al. |
| 2004/0232201 A1 | 11/2004 | Wenchell |
| 2004/0243151 A1 | 12/2004 | Demmy |
| 2004/0267310 A1 | 12/2004 | Racenet |
| 2004/0267311 A1 | 12/2004 | Viola et al. |
| 2005/0006429 A1 | 1/2005 | Wales |
| 2005/0006430 A1 | 1/2005 | Wales |
| 2005/0006431 A1 | 1/2005 | Shelton, IV et al. |
| 2005/0006432 A1 | 1/2005 | Racenet |
| 2005/0006433 A1 | 1/2005 | Milliman |
| 2005/0006434 A1 | 1/2005 | Wales et al. |
| 2005/0023324 A1 | 2/2005 | Doll et al. |
| 2005/0023325 A1 | 2/2005 | Gresham |
| 2005/0067457 A1 | 3/2005 | Shelton |
| 2005/0067458 A1 | 3/2005 | Swayze et al. |
| 2005/0067459 A1 | 3/2005 | Swayze et al. |
| 2005/0067460 A1 | 3/2005 | Milliman |
| 2005/0070925 A1 | 3/2005 | Shelton, IV et al. |
| 2005/0070958 A1 | 3/2005 | Swayze et al. |
| 2005/0072827 A1 | 4/2005 | Mollenauer |
| 2005/0082336 A1 | 4/2005 | Ivanko |
| 2005/0103819 A1 | 5/2005 | Racenet |
| 2005/0119669 A1 | 6/2005 | Demmy |
| 2005/0127131 A1 | 6/2005 | Mastri |
| 2005/0145671 A1 | 7/2005 | Viola |
| 2005/0159778 A1 | 7/2005 | Heinrich et al. |
| 2005/0165415 A1 | 7/2005 | Wales |
| 2005/0173490 A1 | 8/2005 | Shelton, IV |
| 2005/0178813 A1 | 8/2005 | Swayze et al. |
| 2005/0184121 A1 | 8/2005 | Heinrich |
| 2005/0184123 A1 | 8/2005 | Scirica et al. |
| 2005/0184124 A1 | 8/2005 | Scirica et al. |

| | | | | | | |
|---|---|---|---|---|---|---|
| 2005/0184125 A1 | 8/2005 | Marczyk | | 2007/0175949 A1 | 8/2007 | Shelton, IV et al. |
| 2005/0184126 A1 | 8/2005 | Green et al. | | 2007/0175950 A1 | 8/2007 | Shelton, IV et al. |
| 2005/0189397 A1 | 9/2005 | Jankowski | | 2007/0175951 A1 | 8/2007 | Shelton, IV et al. |
| 2005/0192628 A1 | 9/2005 | Viola | | 2007/0175952 A1 | 8/2007 | Shelton, IV et al. |
| 2005/0216055 A1 | 9/2005 | Scirica et al. | | 2007/0175953 A1 | 8/2007 | Shelton, IV et al. |
| 2005/0230453 A1 | 10/2005 | Viola | | 2007/0175954 A1 | 8/2007 | Viola |
| 2005/0263562 A1 | 12/2005 | Shelton, IV et al. | | 2007/0175955 A1 | 8/2007 | Shelton, IV et al. |
| 2005/0279804 A1 | 12/2005 | Scirica et al. | | 2007/0175956 A1 | 8/2007 | Swayze et al. |
| 2006/0000867 A1 | 1/2006 | Shelton, IV et al. | | 2007/0175957 A1 | 8/2007 | Shelton, IV et al. |
| 2006/0000868 A1 | 1/2006 | Shelton, IV et al. | | 2007/0175958 A1 | 8/2007 | Shelton, IV et al. |
| 2006/0011699 A1 | 1/2006 | Olson et al. | | 2007/0175959 A1 | 8/2007 | Shelton, IV et al. |
| 2006/0016853 A1 | 1/2006 | Racenet | | 2007/0175960 A1 | 8/2007 | Shelton, IV et al. |
| 2006/0022014 A1 | 2/2006 | Shelton, IV et al. | | 2007/0175961 A1 | 8/2007 | Shelton, IV et al. |
| 2006/0022015 A1 | 2/2006 | Shelton, IV et al. | | 2007/0175962 A1 | 8/2007 | Shelton, IV et al. |
| 2006/0025809 A1 | 2/2006 | Shelton, IV | | 2007/0175964 A1 | 8/2007 | Shelton, IV et al. |
| 2006/0043147 A1 | 3/2006 | Mastri et al. | | 2007/0179528 A1 | 8/2007 | Soltz et al. |
| 2006/0049229 A1 | 3/2006 | Milliman et al. | | 2007/0187453 A1 | 8/2007 | Smith et al. |
| 2006/0049230 A1 | 3/2006 | Shelton, IV et al. | | 2007/0187454 A1 | 8/2007 | Scirica |
| 2006/0060630 A1 | 3/2006 | Shelton, IV et al. | | 2007/0187455 A1 | 8/2007 | Demmy et al. |
| 2006/0081678 A1 | 4/2006 | Ehrenfels et al. | | 2007/0194079 A1 | 8/2007 | Hueil et al. |
| 2006/0097026 A1 | 5/2006 | Shelton, IV | | 2007/0194080 A1 | 8/2007 | Swayze et al. |
| 2006/0124688 A1 | 6/2006 | Racenet et al. | | 2007/0194081 A1 | 8/2007 | Hueil et al. |
| 2006/0124689 A1 | 6/2006 | Arad et al. | | 2007/0194082 A1 | 8/2007 | Morgan et al. |
| 2006/0138193 A1 | 6/2006 | Viola et al. | | 2007/0221700 A1 | 9/2007 | Ortiz et al. |
| 2006/0138194 A1 | 6/2006 | Viola et al. | | 2007/0221701 A1 | 9/2007 | Ortiz et al. |
| 2006/0151567 A1 | 7/2006 | Roy | | 2007/0278277 A1 | 12/2007 | Wixey et al. |
| 2006/0151568 A1 | 7/2006 | Weller et al. | | 2007/0295780 A1 | 12/2007 | Shelton et al. |
| 2006/0151569 A1 | 7/2006 | Ehrenfels et al. | | 2008/0029570 A1 | 2/2008 | Shelton et al. |
| 2006/0175375 A1 | 8/2006 | Shelton, IV et al. | | 2008/0029571 A1 | 2/2008 | Shelton et al. |
| 2006/0180634 A1 | 8/2006 | Shelton, IV et al. | | 2008/0029572 A1 | 2/2008 | Shelton et al. |
| 2006/0201990 A1 | 9/2006 | Mastri et al. | | 2008/0029573 A1 | 2/2008 | Shelton et al. |
| 2006/0201991 A1 | 9/2006 | Mastri et al. | | 2008/0029574 A1 | 2/2008 | Shelton et al. |
| 2006/0226195 A1 | 10/2006 | Scirica et al. | | 2008/0029575 A1 | 2/2008 | Shelton et al. |
| 2006/0226196 A1 | 10/2006 | Hueil et al. | | 2008/0029576 A1 | 2/2008 | Shelton et al. |
| 2006/0255090 A1 | 11/2006 | Milliman et al. | | 2008/0029577 A1 | 2/2008 | Shelton et al. |
| 2006/0278680 A1 | 12/2006 | Viola et al. | | 2008/0048002 A1 | 2/2008 | Smith et al. |
| 2006/0278681 A1 | 12/2006 | Viola et al. | | 2008/0078800 A1 | 4/2008 | Hess et al. |
| 2006/0289600 A1 | 12/2006 | Wales et al. | | 2008/0078801 A1 | 4/2008 | Shelton et al. |
| 2006/0289602 A1 | 12/2006 | Wales et al. | | 2008/0078802 A1 | 4/2008 | Hess et al. |
| 2007/0023477 A1 | 2/2007 | Whitman et al. | | 2008/0078803 A1 | 4/2008 | Shelton et al. |
| 2007/0027469 A1 | 2/2007 | Smith et al. | | 2008/0078804 A1 | 4/2008 | Shelton et al. |
| 2007/0034669 A1 | 2/2007 | de la Torre et al. | | 2008/0078805 A1 | 4/2008 | Omaits et al. |
| 2007/0034670 A1 | 2/2007 | Racenet et al. | | 2008/0078806 A1 | 4/2008 | Omaits et al. |
| 2007/0045379 A1 | 3/2007 | Shelton, IV | | 2008/0078807 A1 | 4/2008 | Hess et al. |
| 2007/0045380 A1 | 3/2007 | Mastri et al. | | 2008/0078808 A1 | 4/2008 | Hess et al. |
| 2007/0068989 A1 | 3/2007 | Shelton, IV | | 2008/0110958 A1 | 5/2008 | McKenna et al. |
| 2007/0068990 A1 | 3/2007 | Shelton, IV et al. | | 2008/0110961 A1 | 5/2008 | Voegele et al. |
| 2007/0073340 A1 | 3/2007 | Shelton, IV et al. | | 2008/0125812 A1 | 5/2008 | Zubik et al. |
| 2007/0073341 A1 | 3/2007 | Smith et al. | | 2008/0149685 A1 | 6/2008 | Smith et al. |
| 2007/0075114 A1 | 4/2007 | Shelton, IV et al. | | 2008/0164296 A1 | 7/2008 | Shelton et al. |
| 2007/0075115 A1 | 4/2007 | Olson et al. | | 2008/0169327 A1 | 7/2008 | Shelton et al. |
| 2007/0075116 A1 | 4/2007 | Whitman | | 2008/0169328 A1 | 7/2008 | Shelton |
| 2007/0083233 A1 | 4/2007 | Ortiz et al. | | 2008/0169329 A1 | 7/2008 | Shelton et al. |
| 2007/0083234 A1 | 4/2007 | Shelton, IV et al. | | 2008/0169330 A1 | 7/2008 | Shelton et al. |
| 2007/0084896 A1 | 4/2007 | Doll et al. | | 2008/0169331 A1 | 7/2008 | Shelton et al. |
| 2007/0084897 A1 | 4/2007 | Shelton, IV et al. | | 2008/0169332 A1 | 7/2008 | Shelton et al. |
| 2007/0084898 A1 | 4/2007 | Scirica | | 2008/0169333 A1 | 7/2008 | Shelton et al. |
| 2007/0084899 A1 | 4/2007 | Taylor | | 2008/0210738 A1 | 9/2008 | Shelton et al. |
| 2007/0102472 A1 | 5/2007 | Shelton, IV | | 2008/0237296 A1 | 10/2008 | Boudreaux et al. |
| 2007/0102473 A1 | 5/2007 | Shelton, IV | | 2008/0237298 A1 | 10/2008 | Schall et al. |
| 2007/0102474 A1 | 5/2007 | Shelton, IV | | 2008/0277447 A1 | 11/2008 | Smith et al. |
| 2007/0102475 A1 | 5/2007 | Ortiz et al. | | 2008/0283570 A1 | 11/2008 | Boyden et al. |
| 2007/0102476 A1 | 5/2007 | Shelton, IV | | 2008/0283571 A1 | 11/2008 | Boyden et al. |
| 2007/0106317 A1 | 5/2007 | Shelton, IV | | 2008/0283572 A1 | 11/2008 | Boyden et al. |
| 2007/0108252 A1 | 5/2007 | Racenet et al. | | 2008/0283574 A1 | 11/2008 | Boyden et al. |
| 2007/0114261 A1 | 5/2007 | Ortiz et al. | | 2008/0283576 A1 | 11/2008 | Boyden et al. |
| 2007/0114262 A1 | 5/2007 | Mastri et al. | | 2008/0283577 A1 | 11/2008 | Boyden et al. |
| 2007/0119900 A1 | 5/2007 | Ehrenfels et al. | | 2008/0287987 A1 | 11/2008 | Boyden et al. |
| 2007/0119901 A1 | 5/2007 | Ehrenfels et al. | | 2008/0296343 A1 | 12/2008 | Schall et al. |
| 2007/0125826 A1 | 6/2007 | Shelton, IV | | 2008/0296344 A1 | 12/2008 | Cropper et al. |
| 2007/0125827 A1 | 6/2007 | Viola | | 2008/0296345 A1 | 12/2008 | Shelton, IV et al. |
| 2007/0125828 A1 | 6/2007 | Rethy et al. | | 2008/0296346 A1 | 12/2008 | Shelton, IV et al. |
| 2007/0145095 A1 | 6/2007 | Heinrich et al. | | 2008/0296347 A1 | 12/2008 | Shelton, IV et al. |
| 2007/0145096 A1 | 6/2007 | Viola et al. | | 2008/0302854 A1 | 12/2008 | Rethy et al. |
| 2007/0152014 A1 | 7/2007 | Gillum et al. | | 2008/0308601 A1 | 12/2008 | Timm et al. |
| 2007/0158385 A1 | 7/2007 | Hueil et al. | | 2008/0308602 A1 | 12/2008 | Timm et al. |
| 2007/0170225 A1 | 7/2007 | Shelton, IV et al. | | 2008/0308603 A1 | 12/2008 | Shelton, IV et al. |
| 2007/0175947 A1 | 8/2007 | Ortiz et al. | | 2008/0308604 A1 | 12/2008 | Timm et al. |
| 2007/0175948 A1 | 8/2007 | Scirica et al. | | 2008/0308606 A1 | 12/2008 | Timm et al. |

| Publication | Date | Inventor |
|---|---|---|
| 2008/0308607 A1 | 12/2008 | Timm et al. |
| 2008/0314954 A1 | 12/2008 | Boudreaux |
| 2008/0314955 A1 | 12/2008 | Boudreaux et al. |
| 2008/0314957 A1 | 12/2008 | Boudreaux |
| 2008/0314961 A1 | 12/2008 | Boudreaux et al. |
| 2008/0314962 A1 | 12/2008 | Boudreaux |
| 2009/0001121 A1 | 1/2009 | Hess et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001130 A1 | 1/2009 | Hess et al. |
| 2009/0005808 A1 | 1/2009 | Hess et al. |
| 2009/0008424 A1 | 1/2009 | Green |
| 2009/0050671 A1 | 2/2009 | Racenet et al. |
| 2009/0057370 A1 | 3/2009 | Marczyk et al. |
| 2009/0065549 A1 | 3/2009 | Viola |
| 2009/0065550 A1 | 3/2009 | Green et al. |
| 2009/0065551 A1 | 3/2009 | Green et al. |
| 2009/0078738 A1 | 3/2009 | Racenet et al. |
| 2009/0078739 A1 | 3/2009 | Viola |
| 2009/0084826 A1 | 4/2009 | Shah et al. |
| 2009/0090763 A1 | 4/2009 | Zemlok et al. |
| 2009/0090764 A1 | 4/2009 | Viola |
| 2009/0090765 A1 | 4/2009 | Blier et al. |
| 2009/0090766 A1 | 4/2009 | Knodel |
| 2009/0095790 A1 | 4/2009 | Whitman et al. |
| 2009/0101692 A1 | 4/2009 | Whitman et al. |
| 2009/0101694 A1 | 4/2009 | Marczyk |
| 2009/0105535 A1 | 4/2009 | Green |
| 2009/0108048 A1 | 4/2009 | Zemlok et al. |
| 2009/0108049 A1 | 4/2009 | Roy |
| 2009/0114699 A1 | 5/2009 | Viola |
| 2009/0114700 A1 | 5/2009 | Marczyk |
| 2009/0114701 A1 | 5/2009 | Zemlok et al. |
| 2009/0134200 A1* | 5/2009 | Tarinelli et al. ............. 227/180.1 |
| 2009/0261145 A1* | 10/2009 | Heinrich et al. ............. 227/180.1 |
| 2010/0012704 A1* | 1/2010 | Tarinelli Racenet et al. ............. 227/180.1 |
| 2010/0243708 A1* | 9/2010 | Aranyi et al. ............. 227/176.1 |

FOREIGN PATENT DOCUMENTS

| | | |
|---|---|---|
| DE | 2744824 | 4/1978 |
| DE | 2903159 | 1/1980 |
| DE | 3114135 | 10/1982 |
| DE | 4213426 | 10/1992 |
| DE | 4300307 | 7/1994 |
| EP | 0041022 | 12/1981 |
| EP | 0136950 | 4/1985 |
| EP | 0140552 | 5/1985 |
| EP | 0156774 | 10/1985 |
| EP | 0216532 | 4/1987 |
| EP | 0220029 | 4/1987 |
| EP | 0213817 | 11/1987 |
| EP | 0273468 | 7/1988 |
| EP | 0324166 | 7/1989 |
| EP | 0324635 | 7/1989 |
| EP | 0324637 | 7/1989 |
| EP | 0324638 | 7/1989 |
| EP | 0369324 | 5/1990 |
| EP | 0373762 | 6/1990 |
| EP | 0380025 | 8/1990 |
| EP | 0399701 | 11/1990 |
| EP | 0449394 | 10/1991 |
| EP | 0484677 | 5/1992 |
| EP | 0489436 | 6/1992 |
| EP | 0503662 | 9/1992 |
| EP | 0514139 | 11/1992 |
| EP | 0536903 | 4/1993 |
| EP | 0537572 | 4/1993 |
| EP | 0539762 | 5/1993 |
| EP | 0545029 | 6/1993 |
| EP | 0552050 | 7/1993 |
| EP | 0552423 | 7/1993 |
| EP | 0579038 | 1/1994 |
| EP | 0589306 | 3/1994 |
| EP | 0591946 | 4/1994 |
| EP | 0592243 | 4/1994 |
| EP | 0593920 | 4/1994 |
| EP | 0598202 | 5/1994 |
| EP | 0598579 | 5/1994 |
| EP | 0621006 | 10/1994 |
| EP | 0621009 | 10/1994 |
| EP | 0656188 | 6/1995 |
| EP | 0365153 | 8/1995 |
| EP | 0666057 | 8/1995 |
| EP | 0705571 | 4/1996 |
| EP | 0760230 | 3/1997 |
| EP | 1 785 102 A2 | 5/2007 |
| FR | 2542188 | 9/1984 |
| FR | 2660851 | 10/1991 |
| FR | 2681775 | 10/1991 |
| GB | 1352554 | 4/1971 |
| GB | 1452185 | 10/1976 |
| GB | 1555455 | 11/1979 |
| GB | 2048685 | 12/1980 |
| GB | 2070499 | 9/1981 |
| GB | 2141066 | 12/1984 |
| GB | 2165559 | 4/1986 |
| RU | 659146 | 4/1979 |
| RU | 728848 | 5/1980 |
| RU | 980703 | 12/1982 |
| RU | 990220 | 1/1983 |
| WO | WO8302247 | 7/1983 |
| WO | WO 89/10094 | 11/1989 |
| WO | WO9210976 | 7/1992 |
| WO | 9308754 | 5/1993 |
| WO | 9314706 | 8/1993 |
| WO | WO 03094747 A1 * | 11/2003 |

* cited by examiner

STAPLER CARTRIDGE AND CHANNEL INTERLOCK

BACKGROUND

1. Technical Field

This application relates to a surgical stapling device. More particularly, this application relates to an end effector of a surgical stapling device having a cartridge connected to a cartridge channel.

2. Related Art

Surgical stapling or fastener-applying devices are well known, wherein opposing jaw structures grasp and clamp selected tissue, which is then joined by means of surgical fasteners. Typically, one of the jaw members includes a cartridge which houses a plurality of staples arranged in two or more linear rows and the other jaw member includes an anvil having a plurality of staple forming pockets for receiving and forming the legs of the staples. Linear surgical stapling devices, for example, include two elongated jaw members, movable relative to each other, to capture or clamp tissue. When the stapling device is fired on a thick or tough tissue, the cartridge may become displaced from a cartridge channel in which it is contained if the cartridge is not sufficiently secured to the channel.

SUMMARY

The present disclosure pertains to a surgical fastener applying instrument including an anvil, a cartridge assembly defining a longitudinal axis and having a cartridge channel, the cartridge channel having a distal end with at least one protrusion extending transverse to the longitudinal axis, and a fastener cartridge located within the cartridge channel, the fastener cartridge having a plurality of surgical fasteners therein and at least one recess for receiving the at least one protrusion. The position of the fastener cartridge within the cartridge channel may be confirmable through an indicator, e.g., a visual and/or an audible indicator. The cartridge channel may be formed from a material having a bias in one direction such that the cartridge applies a force around the fastener cartridge when the fastener cartridge is positioned within the cartridge channel. The at least one protrusion may comprise a pair of protrusions extending in opposite directions. The pair of protrusions may form a T-shaped extension of the cartridge channel. The at least one recess may form a T-shaped recess corresponding to the T-shaped extension of the cartridge channel. The cartridge channel may be a generally U-shaped channel having a distally-extending extension. The fastener cartridge may have tabs and the cartridge channel may have slots for receiving the tabs.

The various assemblies and their respective internal components of the end effector, when assembled are configured and adapted to facilitate the manipulation, grasping, clamping, fastening, and/or severing of tissue during a given surgical procedure. Particular embodiments of the present disclosure will be described in greater detail with reference to the appended figures in the detailed description to follow.

BRIEF DESCRIPTION OF THE DRAWINGS

The accompanying drawings, which are incorporated in and form part of the specification, illustrate the present disclosure when viewed with reference to the description, wherein.

BRIEF DESCRIPTION OF THE DRAWINGS

Embodiments of the presently disclosed surgical stapling device are described in detail with reference to the drawings, in which like reference numerals designate identical or corresponding elements in each of the several views. As used herein, the term "distal" refers to that portion of the surgical stapler, or component thereof, farther from the user while the term "proximal" refers to that portion of that portion of the surgical stapler or component thereof, closer to the user.

Figure 1:
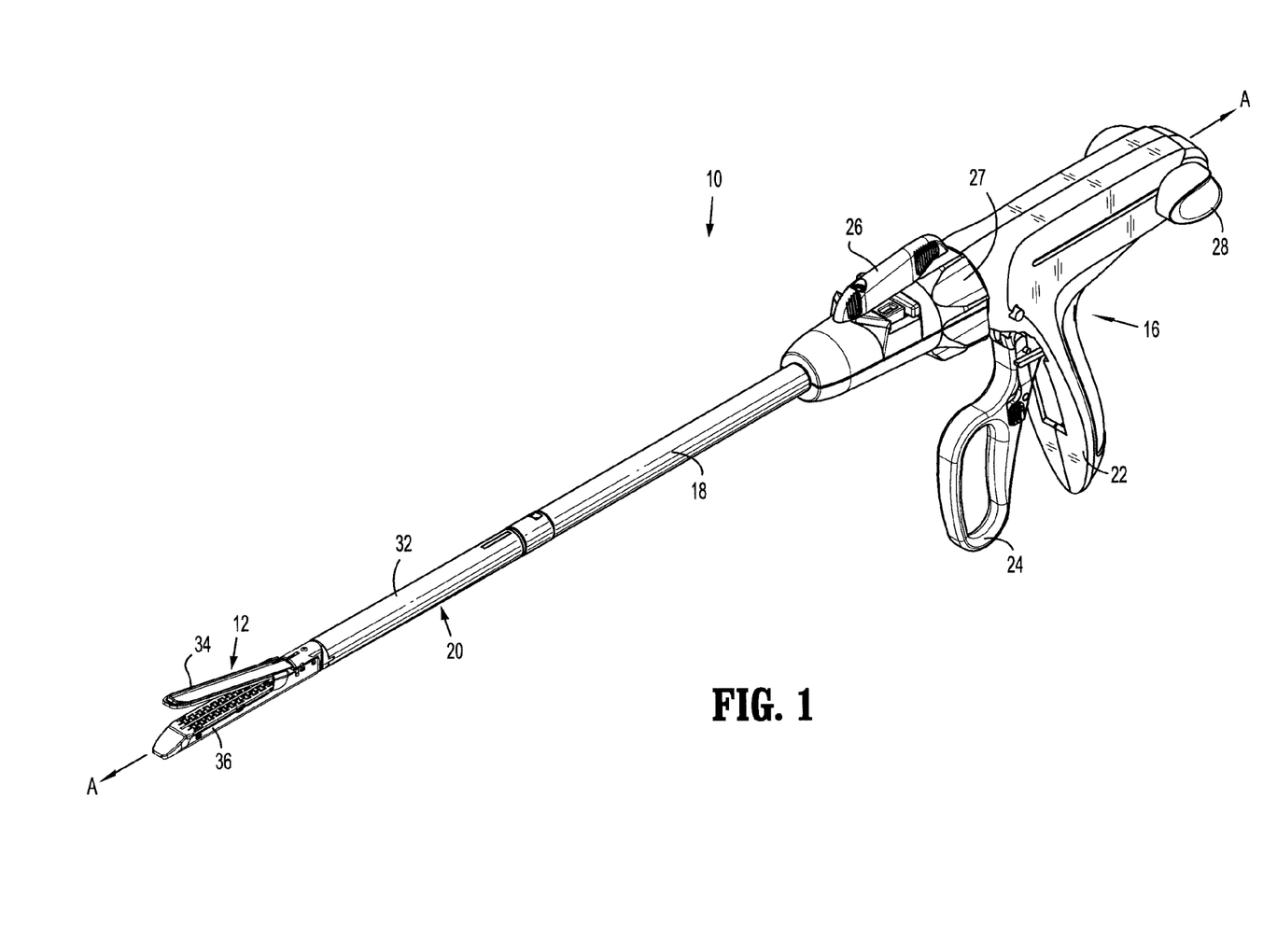
FIG. 1 is a perspective view of a surgical stapling device including one embodiment of the presently disclosed surgical stapling device.

A linear surgical fastener-applying instrument, such as a stapling device 10, shown in FIG. 1, includes a handle assembly 16, an elongated body portion 18 defining a longitudinal axis A-A, and an end effector 12. Many components of the surgical stapling device 10 are substantially as described in U.S. Pat. No. 5,865,361, which is incorporated herein in its entirety by reference. In particular, the handle assembly 16 includes a movable handle 24 and a stationary handle 22. The movable handle 24 is movable through an actuation stroke to clamp tissue and to effect ejection of staples from a staple cartridge of the cartridge assembly 36 included in the end effector 12.

It is contemplated that the presently disclosed embodiments of the presently disclosed end effector and/or cartridge assembly may be used in association with other known linear stapling devices of both endoscopic and open construction. These devices include articulating and non-articulating devices, as well reusable and non-reusable devices. Examples of such devices are disclosed in U.S. Pat. Nos. 6,202,914; 6,250,532; 6,032,849; 5,584,425; 5,413,268; 5,312,023; 5,507,426; 6,953,139, and 5,762,256 which are also incorporated herein in their entirety by reference. Such devices include, but are not limited to, linear stapling devices and laparoscopic or endoscopic surgical stapling devices.

As discussed above, the surgical stapling device 10 includes a handle assembly 16, an elongated body portion 18, and an end effector 12. The handle assembly 16 includes a stationary grip member 22, a pivotable trigger 24, an articulation lever 26, a rotation knob 27, and a return knob 28. In accordance with various embodiments, a loading unit 20 (also known as a "SULU" and/or "DLU") is adapted to be releasably attached to the elongated body portion 18 and includes a proximal body portion 32 and the end effector 12.

The end effector 12 includes an anvil assembly 34 and a cartridge assembly 36 housing a plurality of linear rows of staples. The anvil assembly 34 and the cartridge assembly 36 are pivotable in relation to each other between an open position and a clamped or approximated position where the anvil assembly 34 and the cartridge assembly 36 are in close cooperative alignment. The cartridge assembly has a longitudinal axis and a fastener cartridge or staple cartridge 220. The staple cartridge 220 includes a tissue contacting surface 231 (FIG. 4) which opposes a tissue contacting surface 232 on the anvil (shown in FIG. 2). The tissue contacting surface 232 includes a series of staple forming pockets that are aligned with staple apertures 223 defined in the tissue contacting surface 231 of the staple cartridge 220. The staple cartridge 220 houses surgical fasteners, such as staples, that are supported by pushers within the staple apertures 223 of the cartridge 220. The pushers will be used to drive the staples against the staple forming recesses of the anvil assembly 34 when the cartridge is actuated.

The pivotable trigger 24 is actuable through an actuation stroke or strokes to move the anvil assembly 34 in relation to the cartridge assembly 36 between an open position and a clamped position and to eject staples from the staple cartridge of the cartridge assembly 36. Alternatively, the actuation stroke may pivot the cartridge assembly 36 towards a stationary anvil assembly 34 such that the staples may be formed against staple forming pockets 111.

Figure 4:
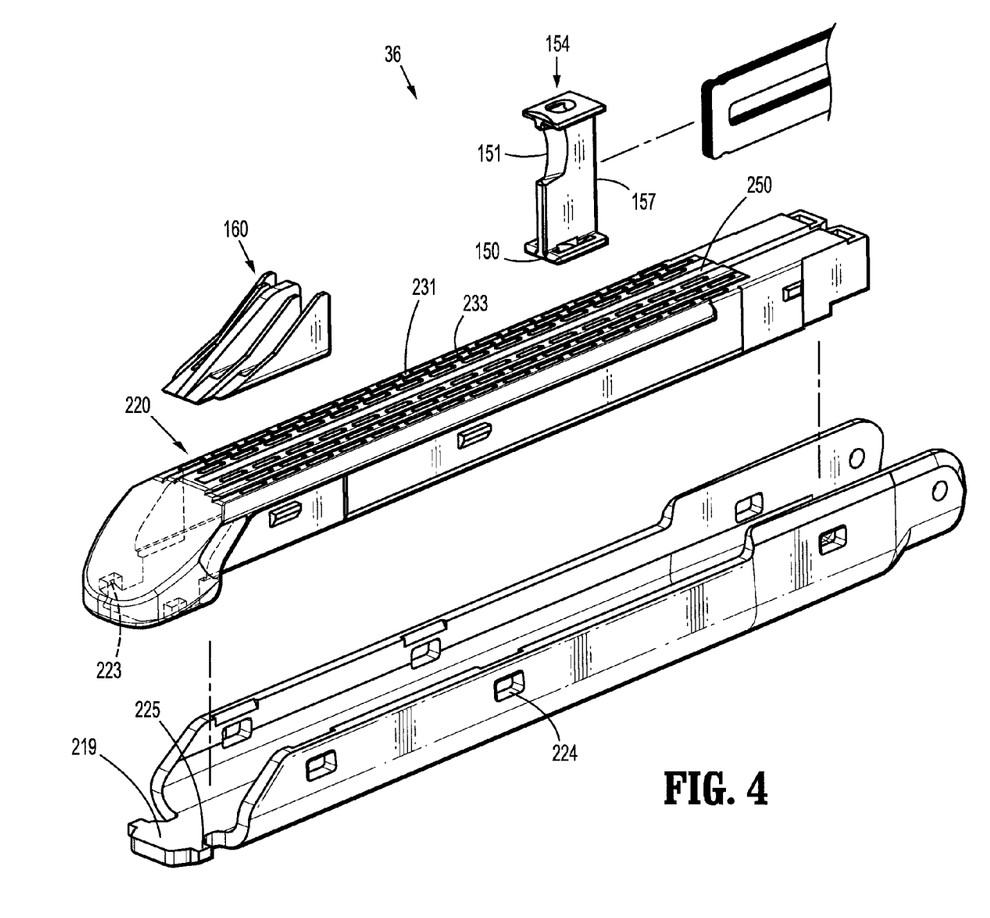
FIG. 4 is an exploded view of a cartridge assembly included in the end effector of FIG. 1.

As seen best in FIG. 4, the surgical stapling device 10 also includes an actuation assembly 150, which may comprise an elongate bar 33 having a blade 151 thereon, and a sled 160. The elongate bar has a distal end with an upper flange 33a and a lower flange 33b. The upper flange engages the anvil assembly 34 and the lower flange engages the cartridge assembly 36. Initially, the elongate bar 33 is moved distally when the pivotable trigger 24 is actuated. A subsequent actuation of the pivotable trigger 24 advances the elongate bar farther. As the sled 160 is positioned distally of the elongate bar, the elongate bar advances the sled 160 through the staple cartridge 220. The sled 160 interacts with the pushers to drive the staples against the staple forming surface of the anvil assembly 34. The pivotable trigger 24 is configured to advance the elongate bar in multiple strokes and may have a pawl that alternately engages and disengages a rack to advance the elongate bar in multiple actuations of the pivotable trigger 24.

Other actuation assemblies are contemplated. These various assemblies and their respective internal components, when assembled allow the linear surgical stapling device 10 to manipulate, grasp, clamp, fasten, and/or sever tissue during a given surgical procedure. The sled 160 is configured to move longitudinally through the cartridge 220 and has wedges to eject the surgical fasteners, such as staples housed within the rows of staple apertures 233. The actuator 150 can include cam wedges or cam surfaces thereon for driving the pushers. The actuator 150 is associated with, e.g., mounted on and rides on, or with or is connected to or integral with and/or rides behind the sled 160. For example, the actuator 150 is disposed or seated in the sled 160 such that after the staples are fired and formed against the staple forming pockets 111 of the anvil assembly 34 (FIG. 2), the blade 151 of the actuator 150 severs tissue between the staple rows as the blade 151 travels through the knife slot 250 of the cartridge 220.

Figure 2:
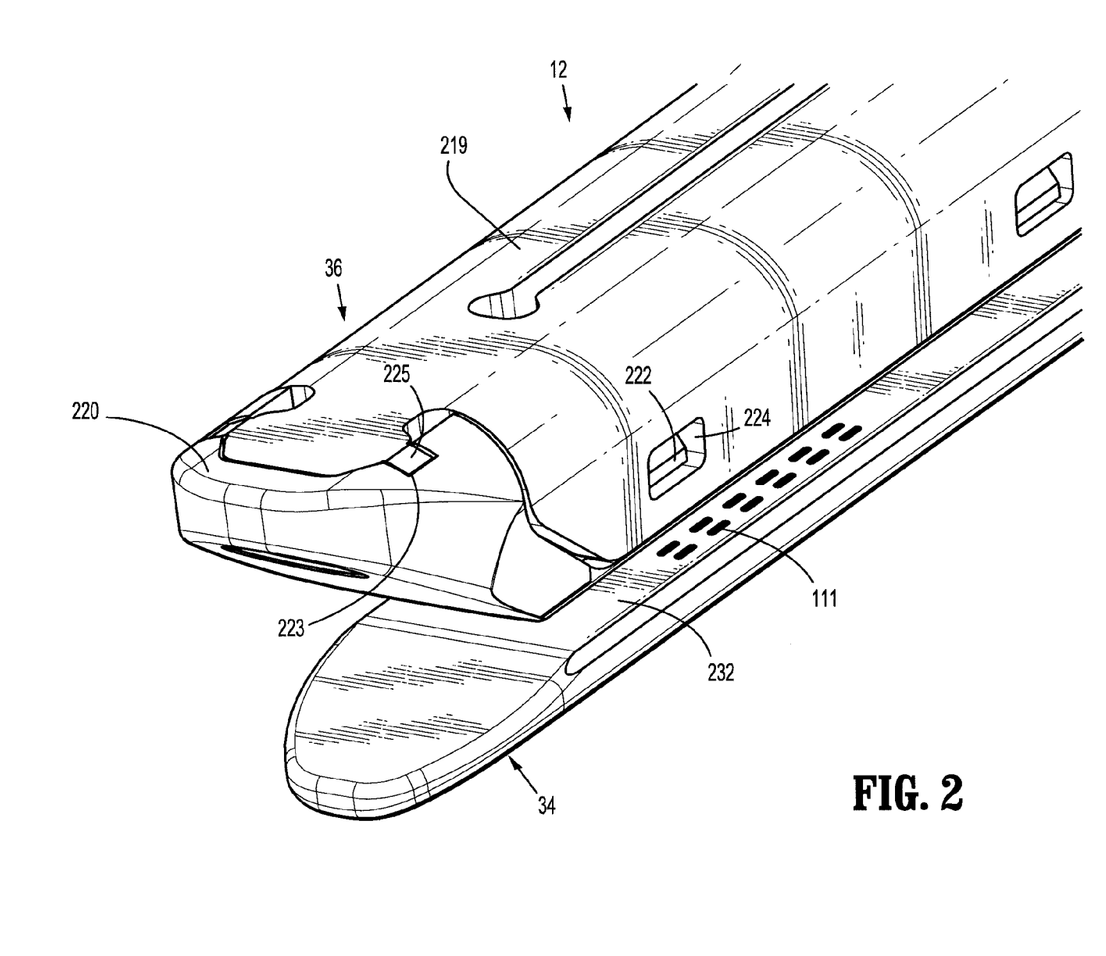
FIG. 2 is an enlarged perspective view of an end effector.

When joining layers of tissue, the anvil assembly 34 and the cartridge assembly 36 may be positioned in a clamped or an approximated position. The end effector 12 may be adapted to access a surgical site through an access device (e.g. a cannula) that is known in the art. To accomplish this, the end effector 12 including the anvil assembly 34 and the cartridge assembly 36, as shown in FIG. 2, is maintained in a clamped or approximated position as the elongated body portion 18 is inserted through a cannula (not shown). Thereafter, the jaws of the end effector 12 (i.e. the anvil assembly 34 and the cartridge assembly 36) are opened such that tissue can be joined and/or cut by clamping and actuating the surgical stapling device 10.

Figure 3:
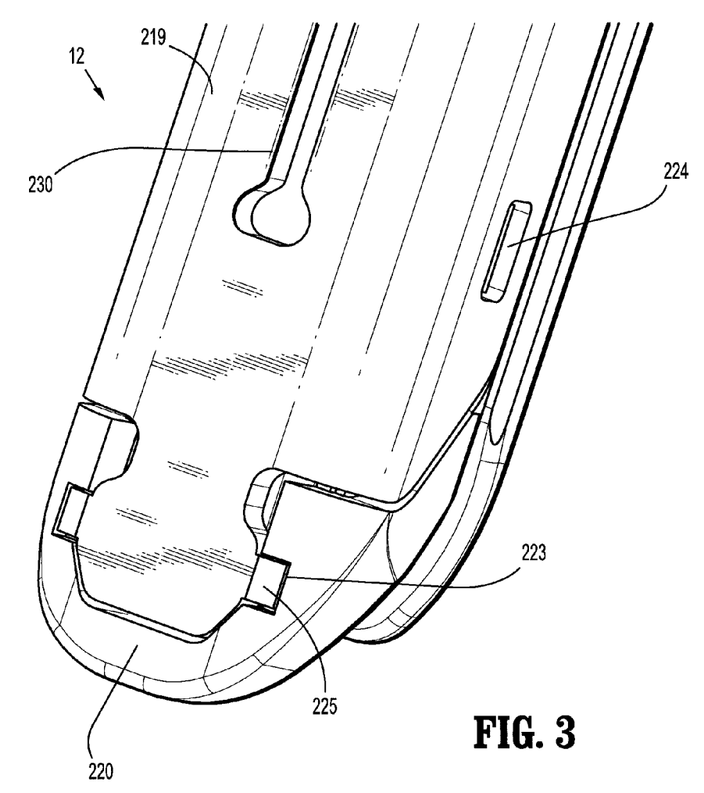
FIG. 3 is an enlarged perspective view of the end effector of FIG. 2.

Now referring to FIGS. 2 and 3, the end effector 12 is illustrated in accordance with an embodiment of the present disclosure. The cartridge assembly 36 may include a cartridge channel 219 and a staple cartridge 220. The cartridge channel 219 is dimensioned and configured to receive the cartridge 220 therein. The cartridge 220 includes tabs 222 formed along either side of the cartridge 220 dimensioned and configured to secure to corresponding slots 224 formed along either side of the cartridge channel 219. The slots 224 are configured to retain, position, and align the tabs 222 of the cartridge therein. A longitudinal slot 230 may extend longitudinally along the top of the cartridge channel 219. The cartridge 220 may include a protrusion, e.g., a fin, configured and adapted to engage the longitudinal slot 230 thereby inhibiting movement of the cartridge 220 relative to the cartridge channel 219. Furthermore, the longitudinal slot 230 provides visual indication of the cartridge 220 with respect to the cartridge channel 219 to facilitate proper alignment of the cartridge 220 relative to the cartridge 220.

The cartridge channel 219 includes protrusions 225 formed at or near the distal end thereof. Recesses 223 formed in the cartridge 220 are dimensioned and configured to engage the protrusions 225, thereby securing and locating the cartridge 220 to the cartridge channel 219. This configuration allows a user to readily determine if the cartridge 220 is securely attached to the cartridge channel 219 and reinforces the connection between the slots 224 and the tabs 222. The protrusions 225 may comprise a pair of protrusions or a single protrusion for being received in a single recess. However, the protrusions 225 desirably form a T-shaped distal end for the cartridge channel 219 and the recesses 223 form a T-shaped recess for receiving the T-shaped extension at the distal end of the cartridge channel 219. In other embodiments, the protrusions 225 and the recesses 223 may be positioned at a more distal end of the cartridge channel 219. The one or more protrusions 225 desirably extend transverse to the longitudinal axis of the cartridge assembly. Transverse, as used herein, includes orientations extending at an angle to the longitudinal axis of the cartridge assembly, and includes orientations extending perpendicular to the longitudinal axis of the cartridge assembly. The cartridge channel 219 may be formed from a material having a bias in one direction, i.e. towards the central longitudinal axis of the end effector 12, such that the cartridge channel 219 applies a force around the staple cartridge 220 when the staple cartridge 220 is positioned within the cartridge channel 219. The protrusions 225 engage recesses 223 to maintain the staple cartridge 220 within the cartridge channel 219 during actuation of the surgical stapling device 10.

In an embodiment, the tabs 222 may have a different color from the cartridge channel 219 to allow the user to visually determine whether the cartridge 220 is properly aligned within the cartridge channel 219. It is contemplated that different colors may also be employed to identify different types of cartridges that may be installed in the end effector 12. Alternatively, the slots 224 may include a colored transparent covering that will appear to change color when the tab 222 is positioned within the slot 224, e.g., if the covering is blue and the tab 222 is yellow, a green color will be perceived by the user when the cartridge 220 is in place. In a further embodiment, when the cartridge 220 is secured to the cartridge channel 219, the user may receive a visual or audible signal to indicate proper alignment, e.g. an audible indication such as a clicking sound.

It will be understood that various modifications may be made to the embodiments disclosed herein. For example, the size, angles and/or curves of the cartridge assembly's surface(s) may be modified to better suit a particular surgical procedure. Therefore, the above description should not be construed as limiting, but merely as exemplifications of various embodiments. Those skilled in the art will envision other modifications within the scope and spirit of the claims appended hereto.

What is claimed is:

1. A surgical fastener-applying instrument, comprising:
   an anvil;
   a cartridge assembly defining a longitudinal axis and having a cartridge channel, the cartridge channel having a distal end including a pair of protrusions extending transverse to the longitudinal axis; the pair of protrusions extending from a distal end of the cartridge assembly and forming a T-shaped; and
   a fastener cartridge located within the cartridge channel, the fastener cartridge having a plurality of surgical fasteners therein and a pair of recesses, each recess configured to receive one of the protrusions, the pair of recesses forming a T-shaped recess corresponding to the T-shaped protrusions extending from the distal end of the cartridge channel, the pair of protrusions releasably receivable within the pair of recesses in an interlocking relationship, each protrusion having a perimeter, the perimeter completely disposed within each recess.

2. The surgical fastener-applying instrument of claim 1, wherein the position of the fastener cartridge within the cartridge channel is confirmable through an indicator.

3. The surgical fastener-applying instrument of claim 1, wherein the cartridge channel is formed from a material having a bias in one direction such that the cartridge applies a force around the fastener cartridge when the fastener cartridge is positioned within the cartridge channel.

4. The surgical fastener-applying instrument of claim 1, wherein the at least one protrusion comprises a pair of protrusions extending in opposite directions.

5. The surgical fastener-applying instrument of claim 1, wherein the cartridge channel is a generally U-shaped channel having a distally-extending extension.

6. The surgical fastener-applying instrument of claim 1, wherein the fastener cartridge has tabs and the cartridge channel has slots for receiving the tabs.

7. The surgical fastener-applying instrument of claim 2, wherein the indicator includes a longitudinal slot extending longitudinally along a top surface of the cartridge channel and a protrusion disposed on the cartridge, the protrusion configured and adapted to engage the longitudinal slot such that placement of the protrusion within the longitudinal slot provides a visual indication of the placement.

8. The surgical fastener-applying instrument of claim 1, wherein the protrusions are tapered to facilitate placement of the fastener cartridge within the cartridge channel.

* * * * *